United States Patent
Fridman et al.

(10) Patent No.: US 8,992,518 B2
(45) Date of Patent: Mar. 31, 2015

(54) METHODS AND DEVICES FOR THE TREATMENT AND PREVENTION OF MALIGNANCY IN ENTERIC DISEASES USING NON-THERMAL PLASMA

(75) Inventors: Gregory Fridman, Philadelphia, PA (US); Danil V. Dobrynin, Philadelphia, PA (US); Alexander Fridman, Philadelphia, PA (US); Gennady Friedman, Richboro, PA (US); Kalyan Chakravarthy, Chelsea, MA (US); Sreekant Murthy, Sewell, NJ (US)

(73) Assignee: Drexel University, Philadelphia, PA (US)

( * ) Notice: Subject to any disclaimer, the term of this patent is extended or adjusted under 35 U.S.C. 154(b) by 798 days.

(21) Appl. No.: 13/256,313

(22) PCT Filed: Mar. 16, 2010

(86) PCT No.: PCT/US2010/027404
§ 371 (c)(1),
(2), (4) Date: Dec. 21, 2011

(87) PCT Pub. No.: WO2010/107741
PCT Pub. Date: Sep. 23, 2010

(65) Prior Publication Data
US 2012/0253265 A1    Oct. 4, 2012

Related U.S. Application Data

(60) Provisional application No. 61/160,577, filed on Mar. 16, 2009.

(51) Int. Cl.
*A61B 18/18* (2006.01)
*A61N 1/40* (2006.01)
*H05H 1/24* (2006.01)

(52) U.S. Cl.
CPC .. *A61N 1/40* (2013.01); *H05H 1/24* (2013.01); *H05H 2245/122* (2013.01)
USPC .......................................................... 606/41

(58) Field of Classification Search
USPC ...................................................... 606/20–42
See application file for complete search history.

(56) References Cited

U.S. PATENT DOCUMENTS

| | | | |
|---|---|---|---|
| 6,099,523 A * | 8/2000 | Kim et al. | 606/40 |
| 2005/0033375 A1 | 2/2005 | Marchal et al. | |
| 2010/0100094 A1 * | 4/2010 | Truckai | 606/39 |

FOREIGN PATENT DOCUMENTS

WO    WO 2006/116252 A2    11/2006

OTHER PUBLICATIONS

Chakravarthy, "Masters Thesis Defense—Therapeutic Evaluation of RDP-58 and Cold Plasma In Vivo in combination with 5 AminoSalisylic Acid—A Study in Mice", Mar. 13, 2009, 1 page.
(Continued)

*Primary Examiner* — Scott Getzow
(74) *Attorney, Agent, or Firm* — Baker & Hostetler LLP

(57) ABSTRACT

Non-thermal plasma is a partly ionized gas, which can be generated by a high-voltage electric field at a low pressure. Disclosed herein are apparatuses and methods for treating an enteric disease in vivo using non-thermal plasma. The disclosed apparatuses have a first conduit comprising a lumen and a tip; a first electrode disposed within the lumen of the first conduit; a second electrode comprised of a metal conduit disposed within the first conduit; an insulator disposed within the lumen of the first conduit, the insulator configured to electrically insulate the first electrode from the second electrode; and a gas channel disposed between the outer surface of the metal conduit and the inner surface of the first conduit, the gas channel being capable of feeding a gas from a gas source to the tip, wherein when the potential is applied, the gas is ionized to produce the non-thermal plasma.

22 Claims, 17 Drawing Sheets

(56) References Cited

OTHER PUBLICATIONS

Fridman et al., "Applied Plasma Medicine", Plasma Process and Polymers, Apr. 2008, 5, 503-533.

PCT Application No. PCT/US2010/27404 : International Preliminary Report on Patentability, Sep. 20, 2011, 6 pages.
PCT Application No. PCT/US2010/27404 : International Search Report Written Opinion of the International Searching Authority, May 19, 2010, 8 pages.

* cited by examiner

| Experiment No: | Primary Mode of Therapy | Concentration and Time of Application | Percentage of DSS (%) | Total No. of Animals | Purpose of Study |
|---|---|---|---|---|---|
| 1A. Plasma Pilot Feasibility Study | CAP Treatment | 0, 4, 30 and 60 seconds | 0 | 12 | To ascertain the toxicity levels in healthy animals due to application of plasma |
| 1B. Plasma Dose Response Study | CAP Treatment | 0, 4, 30 and 60 seconds | 2.5 | 24 | To decide which dosage of CAP is most effective in the model |
| 1C. Plasma as an Adjuvant to 5-Amino Salicylic Acid | CAP Treatment + 5-ASA | 30 seconds, 80 mg/kg per day | 2.5 | 24 | To check the effectiveness of CAP as an adjuvant to 5-ASA treatment |

FIG. 4

METHODS AND DEVICES FOR THE TREATMENT AND PREVENTION OF MALIGNANCY IN ENTERIC DISEASES USING NON-THERMAL PLASMA

CROSS-REFERENCE TO RELATED APPLICATIONS

This application is the National Stage of International Application No. PCT/US2010/027404 filed Mar. 16, 2010, which claims the benefit of U.S. Provisional Application No. 61/160,577, filed Mar. 16, 2009, the disclosures of which are incorporated herein by reference in their entirety.

TECHNICAL FIELD

The disclosed subject matter is in the field of treating enteric diseases. The disclosed subject is also in the field of plasma technology.

BACKGROUND

Inflammatory bowel disorders (IBDs) are characterized by the inflammation of the intestine. Two prevalent forms of the disease are Crohn's disease and Ulcerative Colitis ("UC"). There have been three postulations as to the occurrence of the disorder. They are: reaction to an existent infection in the intestine; defective barrier between mucosa and luminal antigens; and/or a disoriented immune response system by the host's defense mechanism.

All these cases present inflammatory cascade reactions which lead to inflammation in the intestine. The disease instigates a series of steps which start with the breach of the barrier between the intestine and infectious agents. The damaged wall bridges the gulf and exposes the lamina propria immune cells to the internal bacteria and its products. Tissue injury results as the soluble products of activated inflammatory cells come into contact with the bacteria. Therapy to cure and control the disease is preferably designed to block the pro-inflammatory mediators at the end of the cascade as this would decrease the current drift of luminal bacteria and stabilize the immune response.

With specific discussion regarding the colon, the colon is one of the most important portions of the digestive system; in most vertebrates the colon is the last portion of the digestive system. In mammals the colon consists of four parts namely ascending colon, descending colon, transverse colon and the sigmoid colon. The cecum is present at the beginning of the ascending colon and is at an intersection of small and the large intestine. The contents of the large intestine are liquids but they change into solid form as they reach the rectum. The most important functions of the colon are maintaining the water balance absorbing certain vitamins especially vitamin K which is vital for clotting of blood, storing waste and reclaiming water.

As the chyme is processed in the small intestine, 90% of almost all of the nutrients and water are absorbed by the time it reaches the large intestine. As the chyme enters the large intestine the remaining water is absorbed and the chyme is combined with mucus and bacteria and forms the stool. Ulcerative colitis is an inflammatory disorder effecting the mucosa and sub-mucosa of the colon. Ulcerative colitis is one of the chronic inflammatory bowel diseases along with Crohn's disease, Diversion Colitis, Segmental Colitis, Collagenous and Lymphocytic Colitis.

Inflammation is mostly observed in the mucosa and the sub-mucosa. Epithelial cell degeneration is often observed in the tip of the intestinal crypt; the crypt abscess is the initial lesion in UC. This occurs due to the polymorphonuclear leukocytes accumulation within the intestinal crypt tip, the epithelial crypt cells die and chronic inflammatory cells including the neutrophils enter the crypt. The dismemberment of the colon decreases the fluid exchange on its surface leading to abnormal electrolyte absorption, hence creating loose stools. As a result of the inflammation, the vessels of the mucosa and sub-mucosa enlarge and tissue granules develop in the ulcerated part of the intestine, as part of the repair mechanism. The ulcerations destroy the mucosa in highly vascular sections leading to bleeding in the gut lumen. In the next phase, the repair mechanism continues to fill the ulcerations with granulated tissue, which leads to collagen being deposited in the lamina propria, which lead to formation of pseudopolyps as an expression of the granulated tissue causing clinical bowel obstruction.

There are various therapies for UC and Colitis. Sulfasalazine, or Corticosteroids, have been the common form of therapy for the disease for a period of time. Immunosuppressive drugs like 6-mercaptopurine and azathioprine are currently being used in higher number of cases for both active and remittent forms of the disease. Sulfasalazine consists of a sulfapyridine linked to 5-ASA through an azo bond. The drug, after being ingested orally, enters the system and less than ⅓ of the drug is absorbed from the jejunum, a portion of which is excreted through the urine un-metabolized.

The remaining of the un-absorbed portion remains in the small bowel as it is excreted through the bile. The drug moves through the intestine and interacts with the bacterial flora and to a small extent with the distal small intestine and in very little quantities in the colon. The bacteria in the colon cleave the azo bond separating Sulfasalazine, 5-ASA and Sulfapyridine. The sulfapyridine is metabolized by the liver after being absorbed from the colon and is later excreted through the urine. 5-ASA is minimally absorbed from the colon and remains in contact with colonic mucosa and is excreted through the feces. If any of these are taken as single agents without Sulfasalazine, they are absorbed in the jejunum and are excreted and typically do not reach the distal bowel site. As 5-ASA is the only segment reaching the distal colon, it is the active moiety causing the therapy; hence a new class of drugs called aminosalicylates came into play.

5-ASA, which is the active moiety of Sulfasalazine, inhibits both the proliferation of T cells and the production of processed antigens to the T cells. Both 5-ASA and Sulfasalazine inhibit T cells and natural killer cytotoxic effective cells. They also impair addition, chemotaxis, block Interleukin-1 production and of pro-inflammatory cytokines like Tumor Necrosis Factor. Both the compounds 5-ASA and Sulfasalazine inhibit production of cyclooxygenase, prostaglandin, 5-lipoxygenase and 5-lipoxygenase activating protein. Both the agents inhibit the initiation of nuclear factor-KB that plays an important role in activation and increased expression of genes for most of the pro-inflammatory cytokines, chemokines, addition molecules and inflammatory initiators. All of these are crucial perpetrators of development and progress of inflammatory bowel diseases.

There are some current strategies for the prevention and control of the disease, including, but not limited to, Rapidly Metabolizing Steroids, Bismuth Enema, and Probiotics.

SUMMARY

The present subject matter is directed to the treatment of enteric diseases, such as UC and Crohn's disease, through the use of cold or non-thermal plasma. A probe is placed proximate to the treatment site inside the subject to be treated and a non-thermal plasma is generated at the tip of the probe using a power source. The plasma is applied to the location to be treated. The treatment using non-thermal plasma may be supplemented or used in conjunction with treatment using a drug such as 5-Amino-Salicylic Acid.

In some exemplary and non-limiting examples a method of treating an enteric disease is disclosed. A location for treatment is determined A tip of a probe is placed proximate to the location. The probe is configured to generate a non-thermal plasma upon the application of a potential. Once the non-thermal plasma is generated, the location is treated for a period of time and treatment is ended by removing the potential from the probe.

In some exemplary and non-limiting examples, the probe may be constructed from a first conduit comprising a lumen and a tip, a first electrode disposed within the lumen of the first conduit, a second electrode comprised of a metal conduit disposed within the first conduit, an insulator disposed within the lumen of the first conduit, the insulator configured to electrically insulate the first electrode from the second electrode, and a gas channel disposed between the outer surface of the metal conduit and the inner surface of the first conduit, the gas channel being capable of feeding a gas from a gas source to the tip, wherein when the potential is applied, the gas is ionized to produce the non-thermal plasma. The first conduit may be flexible and constructed of various materials such as plastic or glass. In one example, the gas is compressed air.

In some examples, the treatment using plasma may be used in conjunction with treatment using one or more drugs such as, but not limited to, 5-Amino-Salicylic Acid.

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Other features of the subject matter are described below.

BRIEF DESCRIPTION OF THE DRAWINGS

The summary, as well as the following detailed description, is further understood when read in conjunction with the appended drawings. For the purpose of illustrating the subject matter, there are shown in the drawings exemplary embodiments of the subject matter; however, the presently disclosed subject matter is not limited to the specific methods, compositions, and devices disclosed. In addition, the drawings are not necessarily drawn to scale. In the drawings:

FIG. 4 is a table summarizing the experiment setups for testing the use of non-thermal plasma for treating enteric diseases.

DETAILED DESCRIPTION OF ILLUSTRATIVE EMBODIMENTS

Figure 1:
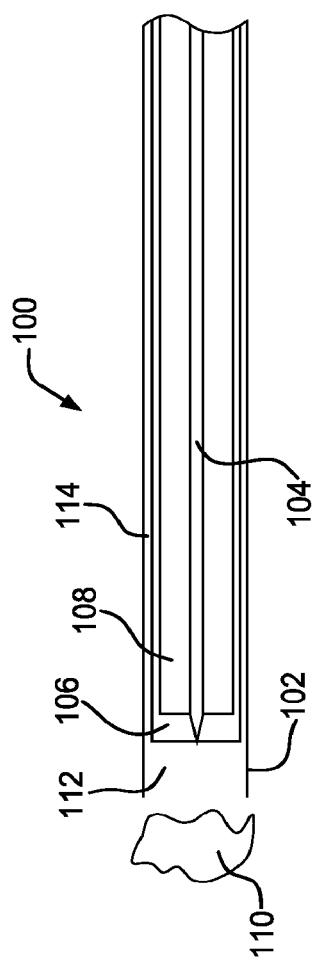
FIG. 1 is a cross-sectional illustration of an exemplary probe for use in treating enteric diseases.

The present subject matter may be understood more readily by reference to the following detailed description taken in connection with the accompanying figures and examples, which form a part of this disclosure. It is to be understood that this invention is not limited to the specific devices, methods, applications, conditions or parameters described and/or shown herein, and that the terminology used herein is for the purpose of describing particular embodiments by way of example only and is not intended to be limiting of the claimed invention.

Also, as used in the specification including the appended claims, the singular forms "a," "an," and "the" include the plural, and reference to a particular numerical value includes at least that particular value, unless the context clearly dictates otherwise. The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

Plasmas, referred to as the "fourth state of matter," are ionized gases having at least one electron that is not bound to an atom or molecule. In recent years, plasmas have become of significant interest to researchers in fields such as organic and polymer chemistry, fuel conversion, hydrogen production, environmental chemistry, biology, and medicine, among others. This is, in part, because plasmas offer several advantages over traditional chemical processes. For example, plasmas can generate much higher temperatures and energy densities than conventional chemical technologies; plasmas are able to produce very high concentrations of energetic and chemically active species; and plasma systems can operate far from thermodynamic equilibrium, providing extremely high concentrations of chemically active species while having a bulk temperature as low as room temperature.

Plasmas are generated by ionizing gases using any of a variety of ionization sources. Depending upon the ionization source and the extent of ionization, plasmas may be characterized as either thermal or non-thermal. Thermal and non-thermal plasmas can also be characterized by the temperature of their components. Thermal plasmas are in a state of thermal equilibrium, that is, the temperature of the free electrons, ions, and heavy neutral atoms are approximately the same. Non-thermal plasmas, or cold plasmas, are removed from a state of thermal equilibrium; the temperature of the free electrons is much greater than the temperature of the ions and heavy neutral atoms within the plasma.

The initial generation of free electrons may vary depending upon the ionization source. With respect to both thermal and non-thermal ionization sources, electrons may be generated at the surface of a cathode due to a potential applied across the electrode. In addition, thermal plasma ionization sources may also generate electrons at the surface of a cathode as a result of the high temperature of the cathode (thermionic emissions) or high electric fields near the surface of the cathode (field emissions).

The energy from these free electrons may be transferred to additional plasma components, providing energy for additional ionization, excitation, dissociation, etc. With respect to non-thermal plasmas, the ionization process typically occurs by direct ionization through electron impact. Direct ionization occurs when an electron of high energy interacts with a valence electron of a neutral atom or molecule. If the energy of the electron is greater than the ionization potential of the valence electron, the valence electron escapes the electron cloud of the atom or molecule and becomes a free electron according to:

$$e^- + A \rightarrow A^+ + e^- + e^-.$$

As the charge of the ion increases, the energy required to remove an additional electron also increases. Thus, the energy required to remove an additional electron from $A^+$ is greater than the energy required to remove the first electron from A to form $A^+$. A benefit of non-thermal plasmas is that because complete ionization does not occur, the power to the ionization source can be adjusted to increase or decrease ionization. This ability to adjust the ionization of the gas provides for a user to "tune" the plasma to their specific needs.

An exemplary thermal plasma ionization source is an arc discharge. Arc discharges have been otherwise used for applications such as metallurgy, metal welding and metal cutting and are known per se. Arc discharges are formed by the application of a potential to a cathode. Arc discharges are characterized by high current densities and low voltage drops. Factors relevant to these characteristics are the usually short distance between the electrodes (typically a few millimeters) and the mostly inert materials of the electrodes (typically, carbon, tungsten, zirconium, silver, etc). The majority of electrons generated in arc discharges are formed by intensive thermionic and field emissions at the surface of the cathode. That is, a much larger number of the electrons are generated directly from the cathode as opposed to secondary sources such as excited atoms or ions.

Because of this intense generation of electrons at the cathode, current at the cathode is high, which leads to Joule heating and increased temperatures of the cathodes. Such high temperatures can result in evaporation and erosion of the cathode. The anode in arc discharges may be either an electrode having a composition identical or similar to the cathode or it may be another conductive material. For example, the anode in arc discharges used in metal welding or cutting is the actual metal be welded or cut.

Although thermal plasmas are capable of delivering extremely high powers, in addition to the electrode erosion problems discussed above, thermal plasmas have additional drawbacks. For example, thermal plasmas do not allow for adjusting the amount of ionization, and thus, they operate at extremely high temperatures. This limits the applications in which thermal plasma may be used to systems that either can withstand the temperatures associated with thermal plasmas or systems having replaceable structures that are damaged by the high temperatures.

Non-thermal plasma ionization sources have alleviated some of the above-mentioned problems. Exemplary ionization sources for non-thermal plasmas include glow discharges, floating electrode dielectric barrier discharges, and gliding arc discharges, among others. In contrast to thermal plasmas, non-thermal plasmas provide for high selectivity, high energy efficiencies, and low operating temperatures. In many non-thermal plasma systems, electron temperatures are about 10,000 K while the bulk gas temperature may be as cool as room temperature.

In one example of a non-thermal plasma, dielectric barrier discharge (DBD) may be utilized using an alternating current at a frequency of from about 0.5 kHz to about 500 kHz between a high voltage electrode and a ground electrode. In addition, one or more dielectric barriers are placed between the electrodes. DBDs have been employed for over a century and have been used for the generation of ozone in the purification of water, polymer treatment (to promote wetability, printability, adhesion), and for pollution control. DBDs prevent spark formation by limiting current between the electrodes. Sample power outputs may be between about 0.5 Watt/cm to about 2 watt/cm.

Various materials can be utilized for the dielectric barrier. These include glass, quartz, and ceramics, among others. The clearance between the discharge gaps is typically between about 0.1 mm and several centimeters. The required voltage applied to the high voltage electrode varies depending upon the pressure and the clearance between the discharge gaps. For a DBD at atmospheric pressure and a few millimeters between the gaps, the voltage required to generate a plasma is typically about 10 kV. Because the plasma that is generated does not appreciably increase the temperature of the surface exposed to the plasma, it may be used for various purposes such as, but not limited to, disinfection, sterilization and plasma therapy.

Plasma therapy may enhance the body's healing and renewal capabilities by providing a support and by not causing a serious tissue or system damage compared to conventional treatment. Because the non-thermal plasma does not apply or impart a significant amount of heat to an area, plasma treatment using non-thermal, or cold, plasma may provide chemical stimulation to the body cells. Although not bound to any specific theory, chemical stimulation may be provided through the generation of a species of radicals within the ionized gas which have a short lifespan. These radicals are highly reactive and have a targeted approach on an area of tissue. Further, these radicals, because of their typically short lifespan, often do not leave an imprint.

Radicals are often present in organisms, playing a role in activating and sustaining various physiological processes. For example, nitric oxide produced by a non-thermal plasma may help to regulate blood vessel function while active oxygen species produced may counter infection at inflammatory sites. Non-thermal plasma may generate the nitric oxide and active oxygen species in an amount that is close to what is naturally generated and, because the plasma can be applied to a specific area, the radicals may be applied in amounts and energies that trigger a chain reaction of cell response without causing extensive oxidative stress.

An issue that is present when subjecting tissue to energized matter is necrosis or accidental cell death. A fatal injury to membrane architecture damage or the leakage of cellular fluids is a direct consequence of necrosis. This results in a counter reaction by the immune system and results in an inflammation at the source of injury. This is a common result in conventional forms of surgery as well as specialized treatments like cryogenic, laser based surgeries.

However, as discussed in more detail below, non-thermal plasma at certain configurations may treat the tissue without accidental cell death, tissue scarring or inflammation at the site of application. There are certain parameters that, among others, may determine the level of plasma action on a living tissue. These parameters include, but are not limited to, exposure time, power and the composition of plasma based on its gaseous environment.

Benefits of in vivo application of plasma inside a living animal may include, but are not limited to a bactericidal effect. Plasma can be used to make the bacteria static or can be used to kill bacteria. This is likely due to the plasma's selective significance to eukaryotic cells as it can remove microbial infection without physically damaging the Meta Structure and architecture of the tissue, a key advantage being the induction of bacterial damage due to the reactive oxygen species induced mechanism.

Another benefit of the application of non-thermal plasma in vivo may be cell detachment and migration. Cell migration is one of the applications of plasma treatment as this causes a temporary detachment of cell adhesives. Cells which are dislodged reattach after a few hours. This may be an added advantage as this phenomenon is typically limited only to a primary layer of the exposed cell. This is likely due to the electrostatic membrane interaction which is facilitated by the plasma electron charge. Another benefit of in vivo application may be cell activation. The results of studies seem to indicate that cells show a definitive increase in the intervals in which they proliferate, adhere and move which mostly explains the great value, this adds to tissue repair.

A further benefit may be apoptosis. Programmed cell death is a critical and important function of a host body as this regulates the death and replenishment of cells. Plasma treatment is effective in inducing apoptosis in a wide range of cells including endothelium, epithelium, smooth muscle and fibroblasts. This is a unique way of reaching nature's modus operandi of disposing off old and dead cells without the side effects of inflammation.

To apply the non-thermal plasma in an area affected by an enteric disease, such as colitis or UC, a probe sized and shaped appropriately is inserted into the affected area. The probe may be inserted either through a body cavity, such as the anus, or through a pathway through surgical means. The non-thermal plasma is generated at a space proximate to and including the tip of the probe to provide for a directed and controlled application of the non-thermal plasma. The researchers have termed the probe to be a Miniature Pin-to-hole Spark Discharge plasma probe or generator.

Referring now to the drawings, wherein like reference numerals designate corresponding structure throughout the views, and referring in particular to FIG. 1, an exemplary cross-sectional illustration of a probe 100 for treating enteric diseases is described. Probe 100 is comprised of hollow, plastic tube 102 which forms a first conduit comprised of a lumen and a tip. Although various types of materials may be used for the conduit, including glass, because of an expected use within the body and a possible need for tube 102 to be flexible, plastic may be a preferred material.

To generate plasma 110, probe 100 has electrode 104 disposed within insulator 108, which is surrounded or encapsulated by metal tube 106, or metal conduit, in this example, acting as a coaxial cathode, or a second electrode. Electrical power (not shown) is applied to electrode 104, metal tube 106 acting as ground. Gas, such as compressed, filtered air, is fed through gap 114. Once power is applied to electrode 104, the gas is preferably ionized. The power source is adjusted to generate a non-thermal plasma. In one exemplary embodiment, the discharge is a specific plasma sphere with a diameter of about 2-3 mm with atmospheric air being fed through gap 114 at 0.2-0.5 atm. The power source is adjusted to provide to electrode 104 a discharge voltage of about 0.5 kV to about 1 kV with a pulse duration of about 50 ms. Further, in this exemplary embodiment, the total power was about 0.1-0.2 W.

Figure 2:
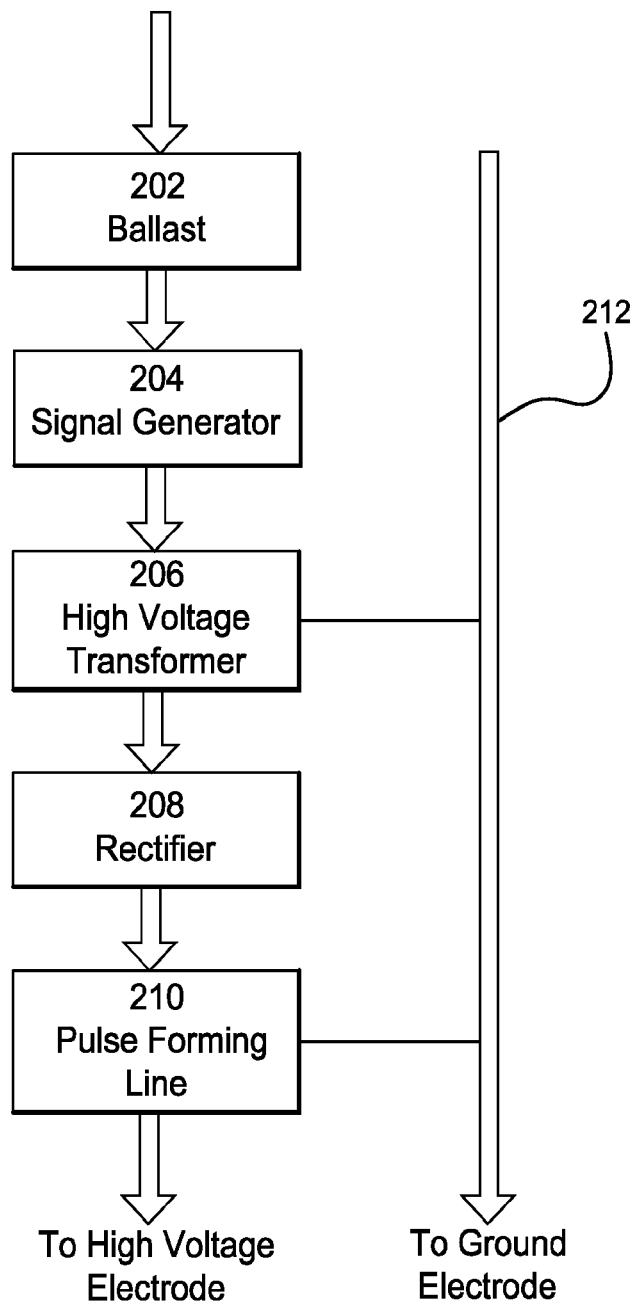
FIG. 2 is a block diagram of a power source for generating a potential used by a probe for use in treating enteric diseases.

FIG. 2 is an illustration of an exemplary power source layout that may be used. An AC current is applied to ballast 202 which, among other functions, acts as a current limiter. The resulting voltage is transmitted to signal generator 204 which may be configured to produce a sinusoidal or pulsed voltage. Although both, and other, types of wave forms may be used, in the present example, a pulsed voltage is used. Although the internal electrical structure of signal generator 204 is not shown, generator 204 may be comprised of one or more capacitors in parallel with one or more electrodes (not shown and not the electrodes of FIG. 1). A typical size of a capacitor is 0.01-1 µF. When breakdown occurs, a short pulse discharge will be formed between the electrodes. In the present example, the pulse duration is several micro seconds with a pulse frequency of about 1-7 Hz.

The pulsed discharge then travels through high voltage transformer 206, rectifier 208 and pulse forming line 210. High voltage transformer 206 and rectifier 208 are used to electrically isolate and transfer the energy between the high voltage electrode, such as electrode 104 of FIG. 1 and the power source of FIG. 2. Pulse forming line 210 receives as an input the pulse from signal generator 204, through the components described above, and stores the energy until an appropriate time, producing a pulse of a certain type (such as a flat topped pulse). In typical configurations, pulse forming line 210 is comprised of charging capacitors that discharge their energy through spark gaps at certain intervals based upon, among other factors, the voltage applied and the capacitance of the capacitors. Ground 212 is provided to various components of the power source of FIG. 2 as well as the coaxial ground of a probe, such as metal tube 106 of FIG. 1.

Figure 3:
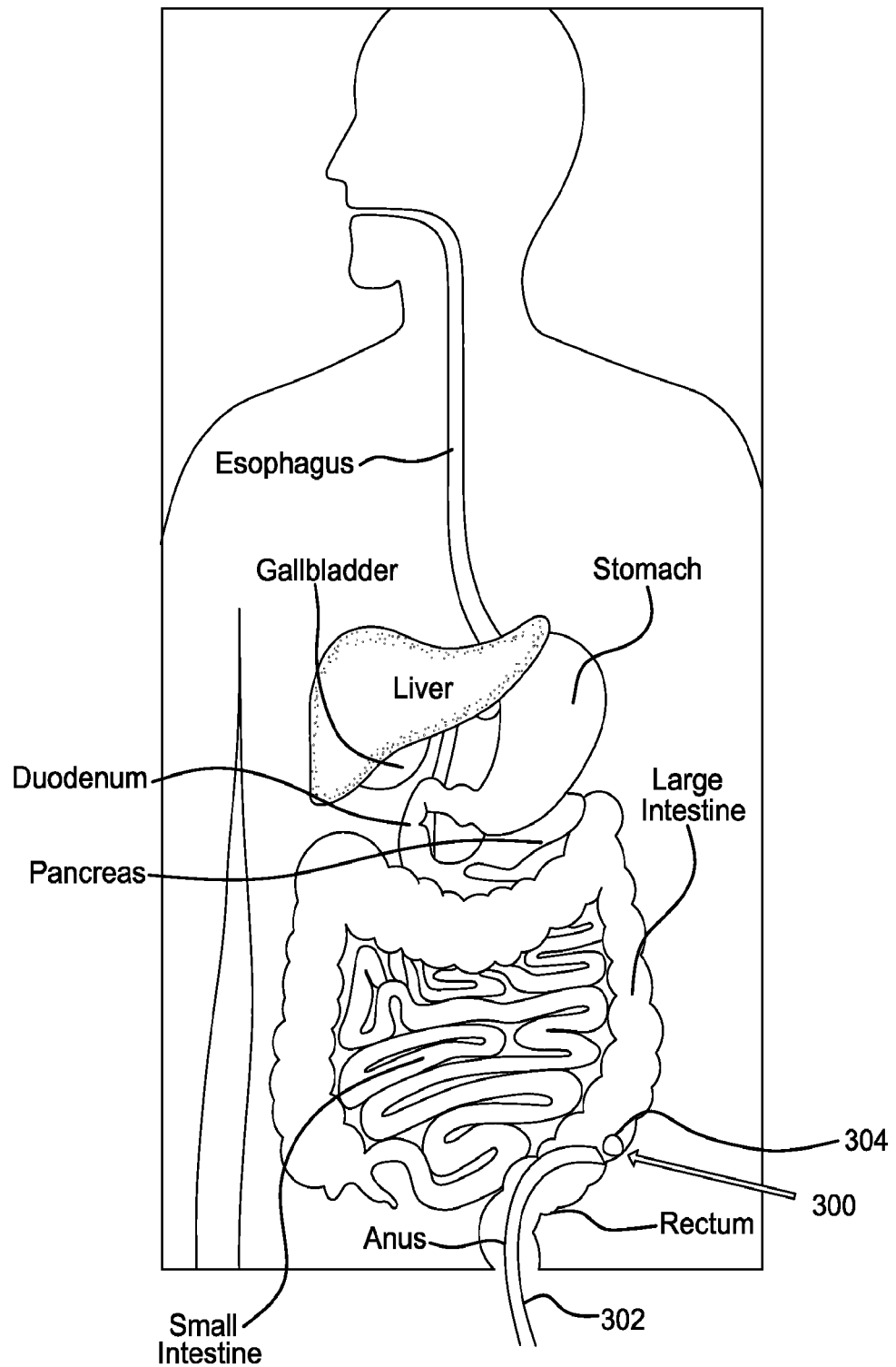
FIG. 3 is a side view illustrating the application of non-thermal plasma to a location to be treated.

FIG. 3 is an exemplary illustration of a human digestive system and the application of a probe, such as probe 100 of FIG. 1, to treat an enteric disease. Location 300 is an exemplary site for treatment using a non-thermal plasma. To treat location 300, probe 302 is inserted through the anus and is placed in a location proximate to location 300 so that plasma 304, when generated, comes in contact with or is in a location proximate to location 300. In this example, probe 302 is constructed and used in a manner similar to probe 100 of FIG. 1. Plasma 304 may be used to treat location 300 either alone or in conjunction with various drugs.

Experiment Setup and Results

To test the present subject matter, a human analogue, mice, were used. Ulcerative colitis was induced into the mice through oral administration of Dextran Sodium Sulphate (DSS) dissolved in water at two different doses of 2.5% and 4%. The mice developed an acute form of inflammation at the third day of the study when they are administered DSS once every day and they have a full disease on the seventh day of the DSS cycle. The other form of disease is chronic inflammation. This is the more advanced stage of the disease. To create this form of the disease, the animals are fed 4% DSS for seven days and then they are given plain water for the next fourteen days, at the end of this cycle they are riveted back to 4% DSS for another seven days. This creates a chronic form of the disease.

The primary characteristics of acute inflammation are increased number of neutrophils in the mucosal layer, shortening of epithelial crypts, hyalination in the lamina propria and this is accompanied with severe weight loss, diarrhea and blood in the stool. Chronic inflammation is typified by regenerating crypt layer and presence of a mixed concoction of macrophages, monocytes and lymphocytes in the mucosal layer. This form of disease gives an opportunity to study the efficacy of drugs and compounds due to its lengthy time period. This protocol, or DSS model, also shows close links to the disease in human beings and also the fact that it is very simple to induce and reproduced weigh in its favor.

Disease Activity Index (DAI) is a measure of the effectiveness of the disease induced by the DSS model. A scale of 0 to 3 was used to quantify the disease with 3 being the most advanced stage of the disease. DAI is scored on the parameters of weight loss, consistency of the stool and presence of blood in the stool. This index indicates a linear correlation with the histology score based on changes in the architecture of the crypt.

Innumerable diseases have an inflammatory response attached to them namely autoimmune, infectious and ischemia perfusions. The progress of disease often leads to an inflammation which is significantly marked by infiltration of the site of injury with neutrophils and macrophages. Hence, this inflammation presents a good opportunity to understand the dynamics and mechanics of complex and intricate diseases. The disease model is a well researched and highly used system to create colitis in mice.

Non-thermal, or cold, plasma was tested both alone and in conjunction with an industry standard colitis curative called 5-Amino-Salicylic Acid. FIG. 4 is a table showing the present study, including the two broad divisions. These divisions, as shown, were divided into two protocols for the first division and into three protocols for the second division. A total of five whole experiments were conducted. The primary objective of the study was to understand the mechanism and modus operandi of the disease colitis in a DSS induced model of mice. In all the experiments Female Swiss Webster mice approximately aged to eight weeks of 25 to 30 grams in weight were used. All these animals were housed in separate cages based on their groups in the animal facility at Drexel University College of Medicine.

The most important and critical part of the whole study is the evaluation of disease prevalence in the animals induced with colitis. As discussed above, the disease progression is measured using the Disease Activity Index. The DAI in animals is scored by a cumulative add-up of body weight, hemocult reactivity, stool consistency and presence of visible blood in the stool. The DAI floats on a scale of 0-3 where 0 represents least clinical disease and 3 represents most prevalent severe disease. In the present study, the DSS model takes the DAI to a score of 3.0 on day 7 or 8. The chronic study takes a bent of 3.0 DAI in recurring cycles. During the whole length of the study, animals were monitored everyday for changes in weight, stool consistency and appearance of gross bleeding.

The first part of the study was to understand how the application of non-thermal plasma affects biological tissue. The primary objective of the study was to ascertain if non-thermal plasma, or cold atmospheric plasma (CAP), administered in vivo in mice would cause any damage to the cells, tissue or the animal itself. Twelve animals were anesthetized and four doses (0 seconds, 4 seconds, 30 seconds, and 60 seconds) of plasma was discharged, in three animals per group. Tissue damage was ascertained by Evans Blue (EB) extravagation. Mass Spectrometry of the saline fluid collected from the colon showed no trace of EB, showing that plasma did not affect the tissue architecture or constitution. This may be due to the fact that the temperature of CAP is just slightly over room temperature, thus not causing appreciable damage to the tissue, colon or the animal.

After it was observed that plasma does not appreciably damage the tissue, the next step was to check the most efficient dosage of plasma. In that study, 12 animals were divided into 4 groups each receiving 0, 4, 30 and 60 seconds of CAP every alternate day for 7 days. All the animals were fed 2.5% DSS for 7 days in parallel with plasma treatment. DAI was scored everyday to see which dosage of plasma was most effective in controlling the rampage of the disease. For the plasma probe to be inserted and to go through the colon, the colon has to be cleansed of stool specks. To do so, the animals were fed a polyethylene glycol based laxative along with DSS on days before plasma treatment. However, the stool consistency on the next day was compromised as the laxative made the stool consistently loose. Hence, the data extracted from the study was bifurcated and was analyzed using a three pronged approach considering weight, stool consistency and presence of blood in the stool, weight and presence of blood in the stool (without stool data), and mean Hemoccult (visible blood in the stool).

Figure 5:
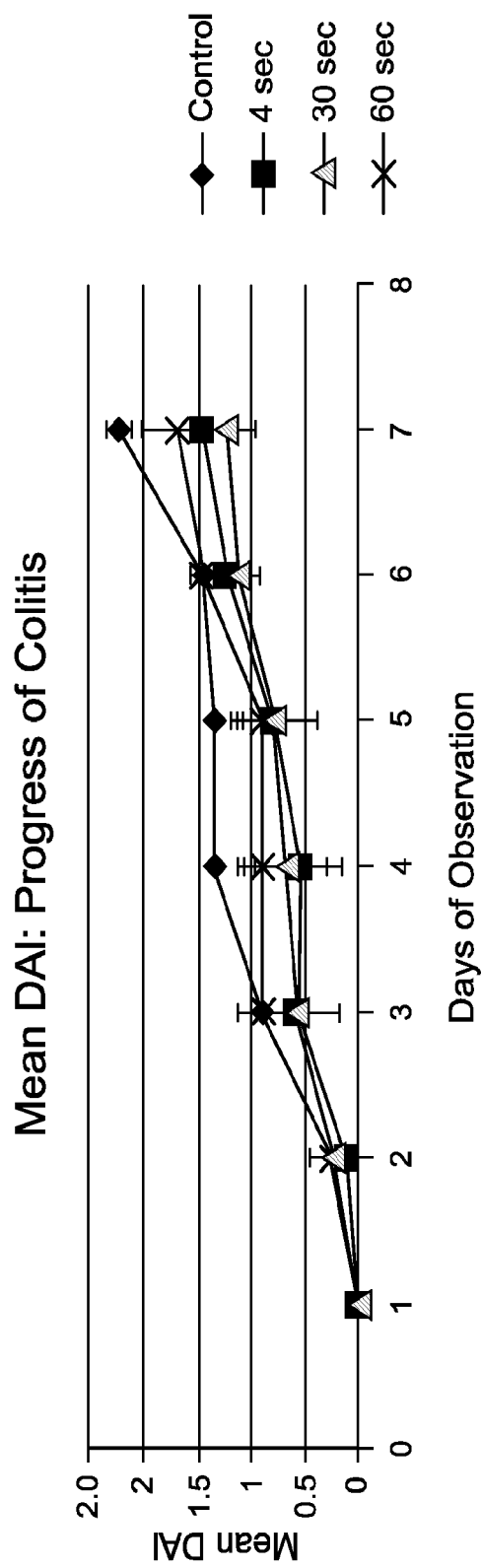
FIG. 5-17 are graphs showing testing data for various testing configurations to illustrate the results of using a non-thermal plasma for treating enteric diseases.

FIG. 5 illustrates the progress of colitis for each dosage time. It should be noted that the graph of FIG. 5, and the following graphs, consider weight, stool consistency and presence of blood in the stool. The scatter plot of FIG. 5 illustrates the DAI graphed against the days of observation of the animals during the 7 days of the study. The animals were fed 2.5% DSS ad libitum, for 7 days and four doses of plasma were administered every alternate day.

The data shows that, in the control group the DAI scored using weight, stool consistency and blood visibility in the stool reaches a value of 2.3 by the end of 7 days. It grows gradually from 0 on day 1 and consistently goes up to 2.3 on the DAI scale. As this group did not receive any drug or plasma treatment, the trend line will be used as a reference mark for the other groups. The group which received 60 second plasma reached a DAI of 1.6 on day 7. Hence, the disease is not controlled very well in the 60 second plasma group. On days 3, 4 and 5, the 60 second pulse stabilized the disease and prevented it from growing. However, as the severity of the disease increased the pulse ceased to work effectively. This could be due to the assumption that over exposure of plasma might not be very useful in controlling the disease.

The 4 second plasma pulse data shows disease reduction capability during the end stage of the study and it is comparatively better than the 60 second pulse. It shows good disease control through the course of the study. The most efficient dosage of plasma as shown by the study is that of the 30 second pulse. This group shows high resilience against the progression of the disease and as compared to the control, shows great ability in stopping the growth of the disease even when DSS is being fed in parallel. The maximum DAI in this group is 1.2 as observed on day 7, the day of maximum disease prevalence. We can infer that this is the optimum dose of plasma, based upon the testing conditions, to effectively control the disease.

Figure 6:
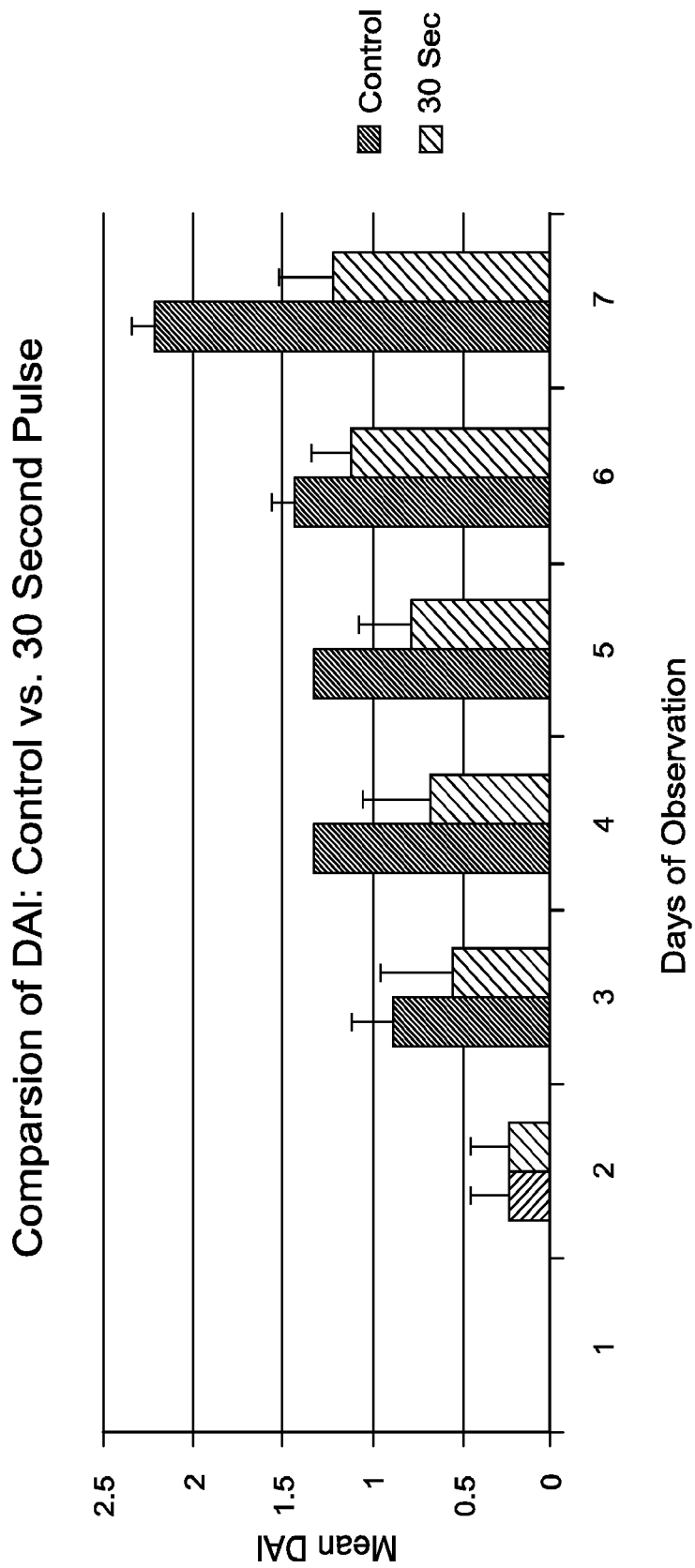

The 30 second pulse was tested further with the data illustrated in the bar graph of FIG. 6. The graph shows a comparison of the DAI for the control versus the 30 second pulse. The mean DAI is on the Y-axis and the days of observation on the X-axis. The two groups of control which received no plasma treatment and the 30 second plasma exposure group are represented in form of disease progression. It may be seen that there is a credible difference between the disease activities in the two groups. The plasma group curtailed the disease and did not allow the DAI to go over 1.2 even on the day of maximum disease prevalence. The 30 second plasma exposure group shows the most effective plasma treatment compared to the control, 4 sec and 60 sec dosage. The data indicates that, under the present testing conditions, a plasma discharge of 30 second is an effective in controlling the spread of colitis.

Figure 7:
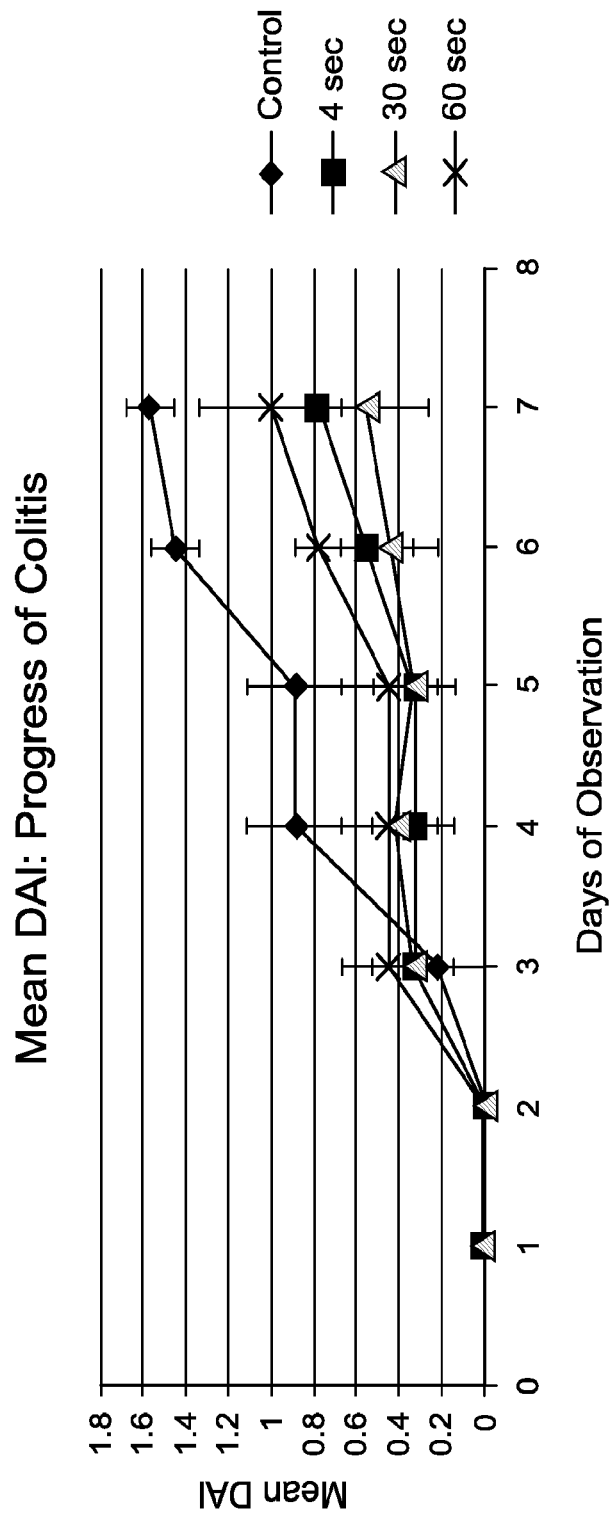

FIG. 7 comprises the same data as FIG. 5 but with an added trend line to show the trend of the disease progression. The data is represented with mean DAI on the Y-axis and days of observation on the X-axis. Four groups of animals have been considered in the experiment and it is observed as a tweak on the earlier graph as only the changes in weight and hemoccult have been considered while generating the graph as the laxative that was administered to the animals on days prior to plasma treatment might have compromised the score based on stool consistency as this makes the stool comparatively loose. The graph shows very clearly the extent to which the 30 second plasma group controls the DAI compared to the other groups of the study. The DAI on the new scale reaches a high of 1.5 on the control group but is at a range of near 0.5 on the 30 second plasma exposure group. The renewed vantage point clearly explains the visible difference between the four groups as the absence of stool data also confirms the fact that 30 second plasma exposure group worked well compared to the control in the current study.

Figure 8:
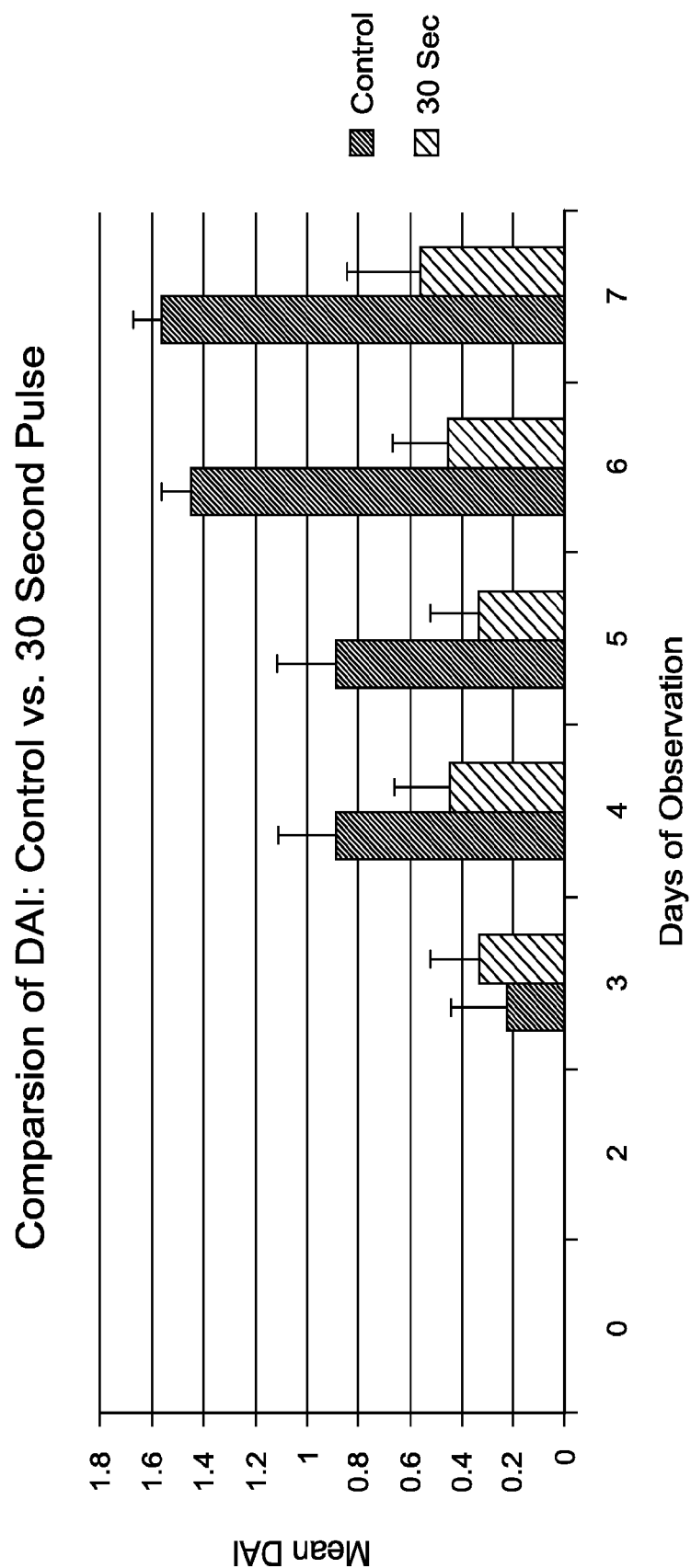

FIG. 8 illustrates the results of a comparison of the DAI of a control group versus a group receiving 30 second pulses with mean DAI on the Y-axis and the days of observation on the X-axis for a span of seven days. The 30 second plasma group very clearly has a low prevalence of DAI even on days when the disease is projected to be sizable as it stops the DAI from going over 0.5 even on the ultimate and penultimate days. On comparison, the DAI in the control group reach a high of 1.5 on the final day of the study. This further shows that there is a consistent difference between the two extremes of groups.

Figure 9:
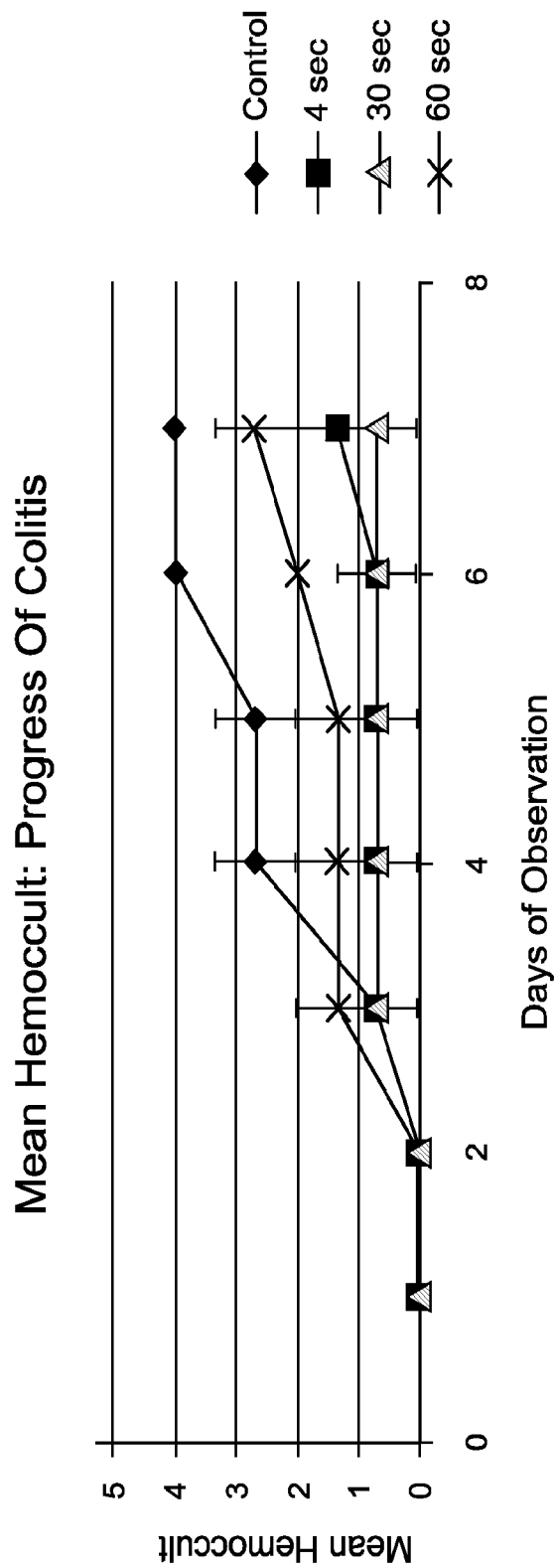

FIG. 9 is a scatter plot with the X-axis as the days of observation and the Y-axis as the mean hemoccult. In this set of data, only the presence of visible blood in the stools has been considered as the primary responsibility of plasma is to coagulate the blood inside the inflamed colon. As the prime facet of tissue degradation of colitis is through bleeding out of the tissue which can be observed on the stool study. Hence this data is important to check if plasma can actually clot and coagulate the blood inside the colon.

The data shows that there is a significant difference statistically between the control group and the 30 second plasma group, as the visible blood in the stool index shows that on the final days of study hemoccult reaches a high of 4 in the control group vis-à-vis the 30 second group has a DAI of just over 0.5. It can be inferred from the data that the 30-second plasma group is showing blood coagulation inside the colon along with the 4 second plasma group with 30 second group being a lot more effective on the final day of the study.

Figure 10:
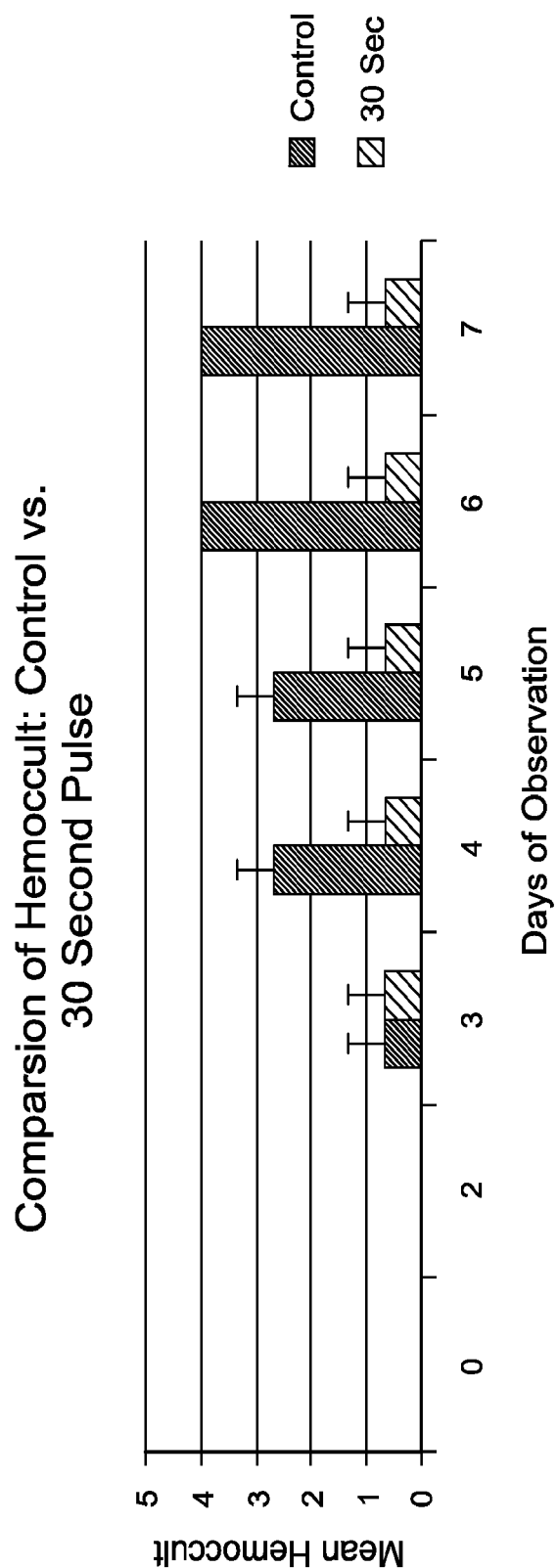

FIG. 10 shows a comparison of hemoccult in the control group versus the group receiving a 30 second pulse. The bar graph shows the mean hemoccult on the Y-axis and the days of observation on the X-axis. The groups show a statistically significant difference in the presence of blood in the stool samples. Days 6 and 7 witness a significant difference between the two bars with mean hemoccult reaching 4.0 in the control group when the hemoccult is at 0.6 on all days 4, 5, 6 and 7 in the 30 second group.

Figure 11:
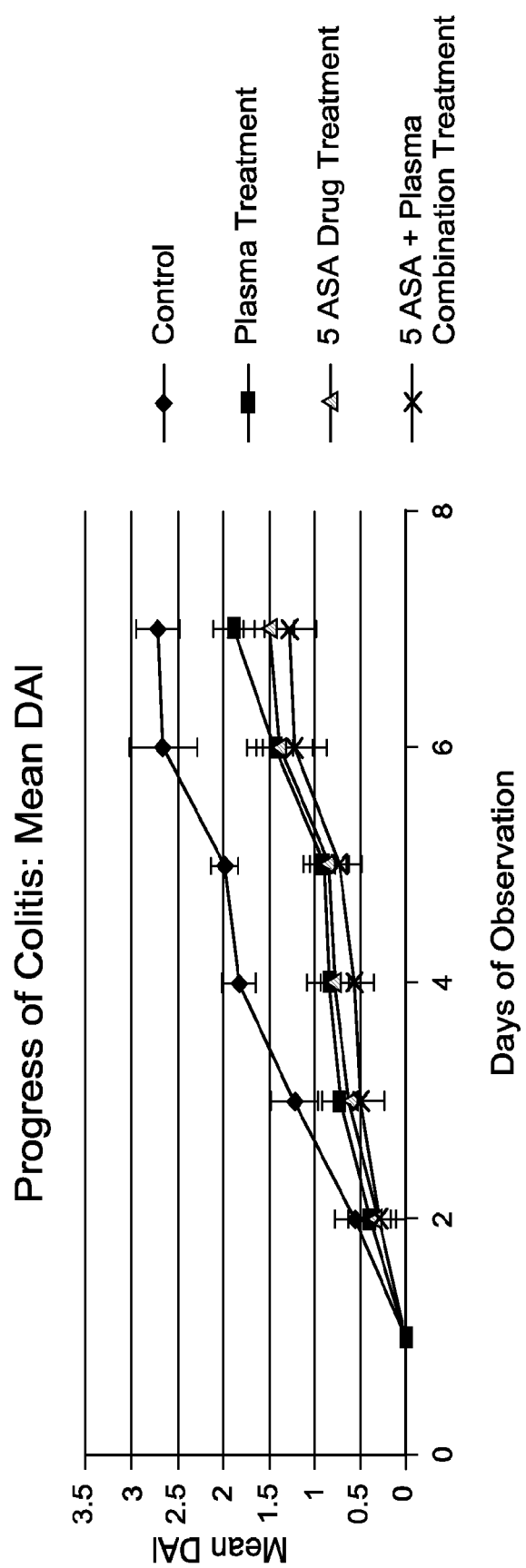

As discussed earlier, for various reasons, non-thermal plasma may be used in lieu of or in conjunction with drug treatment. In this following test, 5-Amino-Salicylic Acid, a common UC treatment drug, was tested against plasma treatment, no treatment and plasma plus 5ASA. FIG. 11 shows the progress of colitis for the various treatments (or no treatment in the case of the control). The chart of FIG. 11 shows the scatter plot of the data mined for this part of the study. The graph shows the progress of colitis expressed with mean DAI on the Y-axis and days of observation on the X-axis.

All the four groups show a linear increase in the disease as the days progress. However, there is an appreciable demarcation between the four groups of study. The control group as always shows a steady increase through the course of seven days with the DAI reaching an expected 2.7 on day 7. The plasma treatment group was administered 30-second plasma pulse and the data is in direct correlation with the data acquired in the previous study and it also shows a constant increase. However, the disease is curtailed to near 1.8 on the DAI scale. 5-ASA treatment group received the drug only without the plasma pulsing. Because 5-ASA is an industry standard in curing the disease, the spread of colitis is controlled and has a statistical significance over the control on days 5, 6 and 7.

The final group was designed and was administered the drug 5-ASA along with the plasma pulsing on every alternate day. The group showed very positive results as both in combination proved to be effective in controlling the disease and keeping the DAI on a level of 1.2 on the DAI scale. This is a sizable variation as compared to the control group and there is a difference of one whole point between both of them with a statistical significance observed on days 4, 5 6 and 7.

Figure 12:
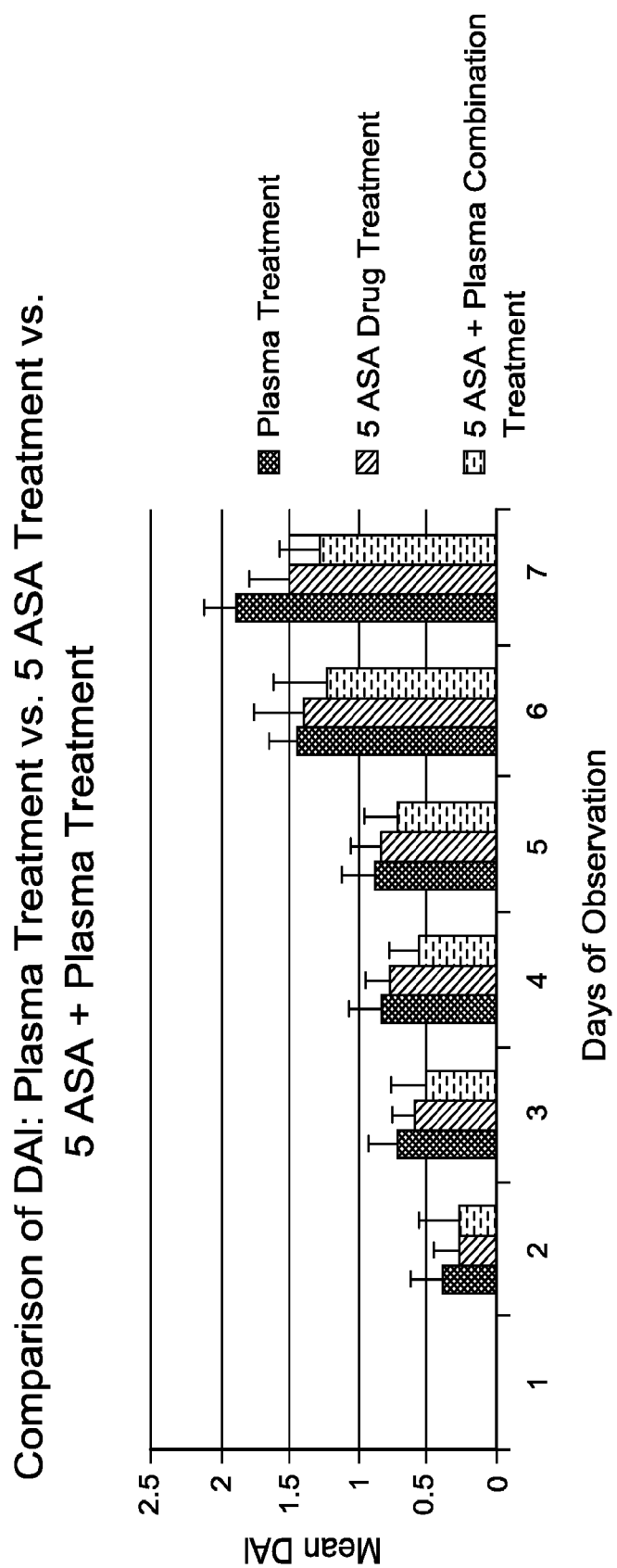

FIG. 12 is a graph which is an extension of the graph shown in FIG. 11. The graph of FIG. 12 shows the variation in the DAI levels of the three doses of treatment. Plasma treatment alone shows certain disease control capability and the combination treatment shows very good results on the final day even when the disease is at its peak.

Figure 13:
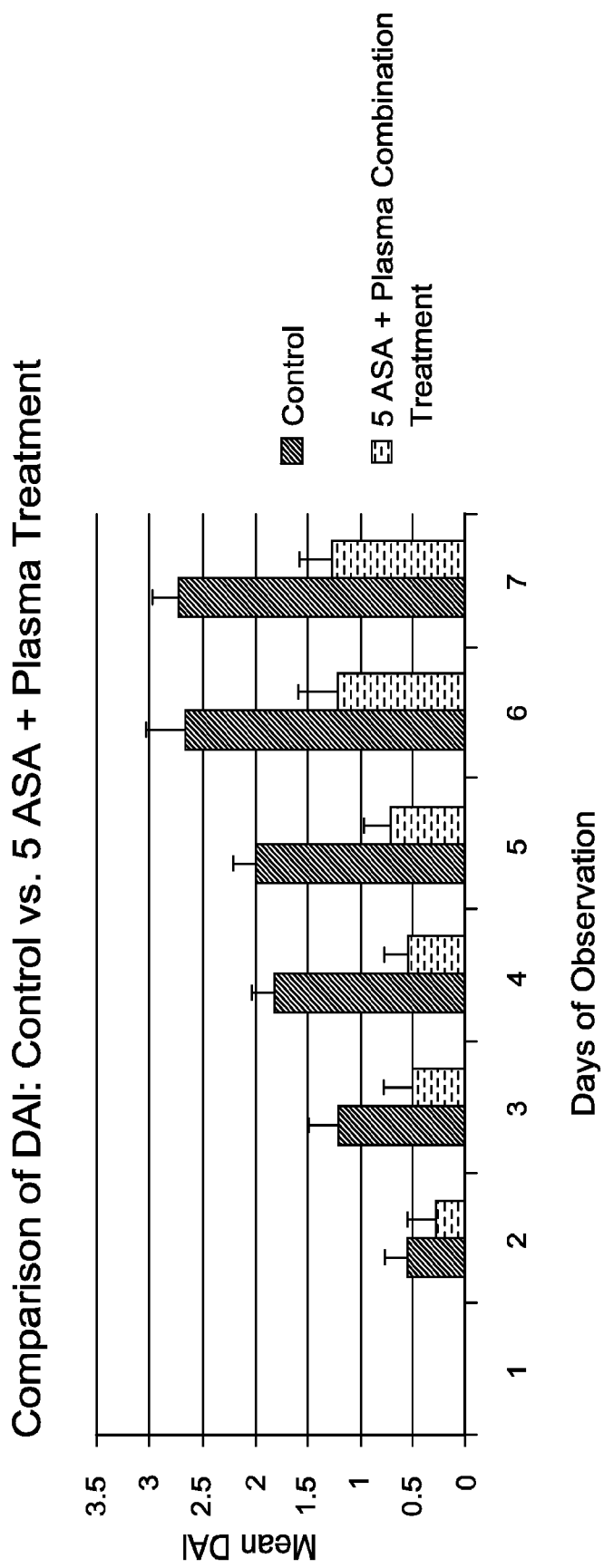

FIG. 13 is a graph showing a comparison of a control group receiving no treatment versus a group receiving a combined plasma and 5-ASA treatment. The graph shows the variation in the control and the treated group as this is a statistically significant variation, it is inferred that the treatment has been effective in keeping the rampage of the disease at bay. Although not intending to be bound to any particular theory of operation, this could be due to the fact that plasma takes care of the sterilization and coagulation of the blood in the colon and 5-ASA controls the disease by its tinkering of the biological pathway which mediates the progress of the disease.

Figure 14:
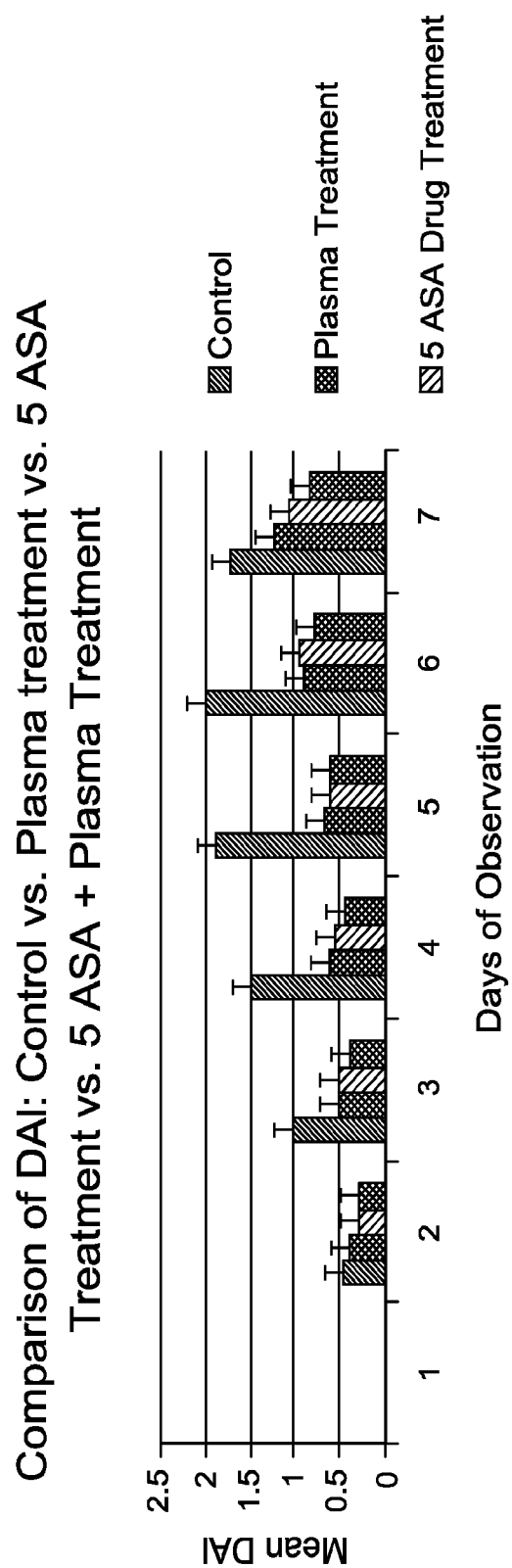

FIG. 14 is a bar graph showing a comparison of DAI between a control group receiving no treatment, a group receiving plasma only treatment, and a group receiving plasma and 5-ASA treatment. The bar graph shows the DAI values of the four groups under consideration and is plotted against mean DAI on the Y-axis and the days of observation on the X-axis. The four groups show a variation on days 4, 5, 6 and 7. It was observed that the groups receiving the treatment of plasma, drug and their combination show a disease reduction capability, even when the stool consistency is not considered. This further illustrates that the plasma has an application in coagulating the blood in the inflamed colon and that the disease can be controlled with direct contact with the area affected with minimal to no interaction with the biological pathways.

Figure 15:
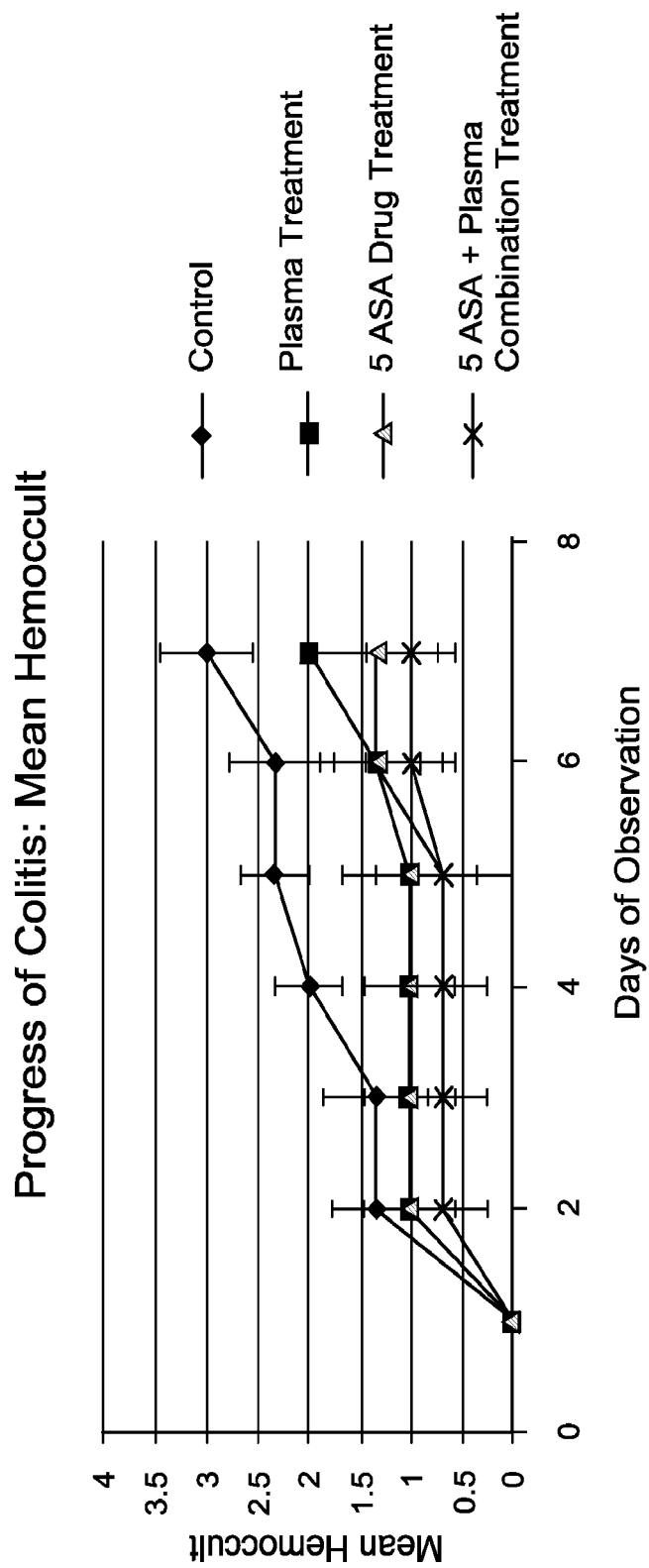

FIG. 15 is a graph illustrating any detection of blood in the stool of the tested groups. The scatter plot is designed to express the mean hemoccult charted on a scale of 0 to 4 with 4 being the advanced stage of the disease. The mean hemoccult is plotted on the Y-axis and the days of observation are plotted on the X-axis. The objective of this line of analyzing the data is to check the hypothesis that plasma treatment has an effect on the blood observed in the stool. The mean hemoccult only shows the presence of blood in the stool and does not consider any other parameter. The plasma treatment shows a significant drop in the hemoccult scale as compared to the control which shows that plasma actually is working in clotting the blood that is being pumped out of the inflamed region in the colon. The combination treatment further reduces the hemoccult score as a two pronged approach is taken against the disease.

Figure 16:
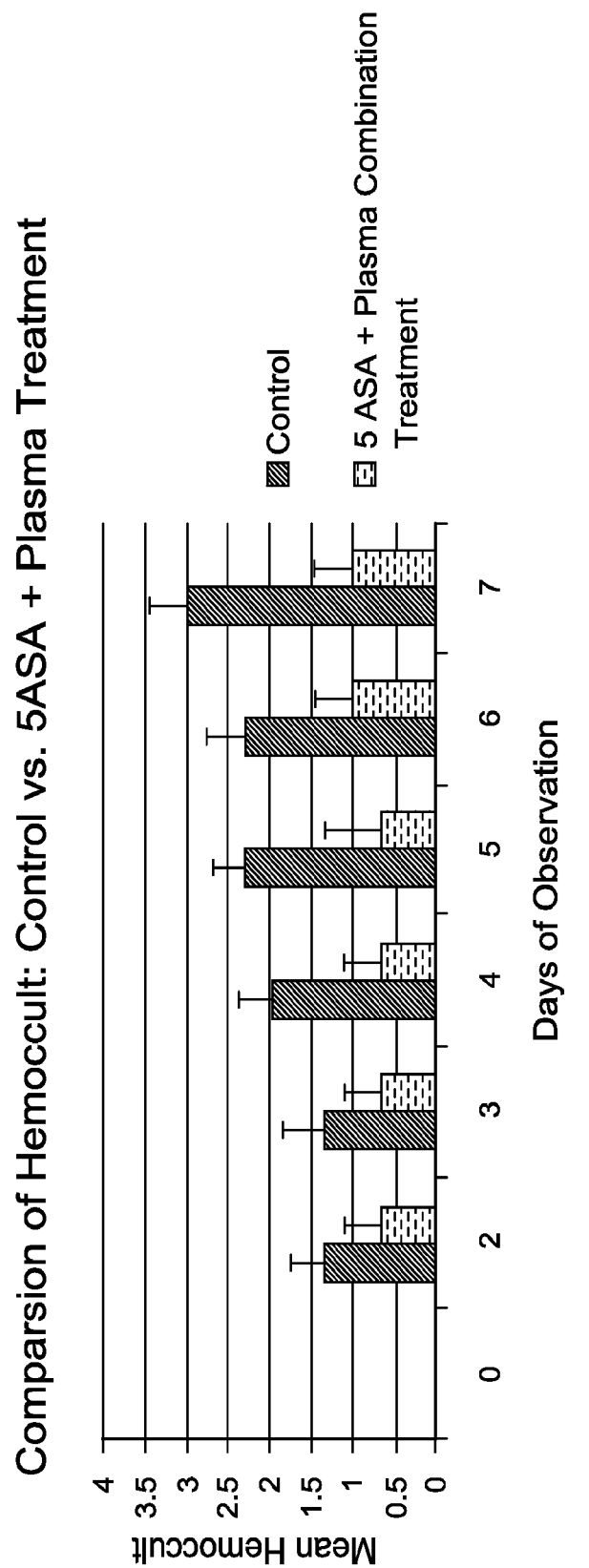

FIG. 16 is a graph showing a comparison of hemoccult between a control group and a group receiving 5-ASA drug treatment. The bar graph shows the mean hemoccult score on the Y-axis and the days of observation on the X-axis. The data portrayed here shows that the drug is effective in controlling the bleeding from the colon as this drug regulates the biopathways responsible for the inflammation. A disease reduction by the drug has a direct relevance to the amount of blood oozing out of the colon as the drug is tested already to be effective in controlling the disease. It is observed that its mechanism is by regulating the system into clotting the blood from the inside and by curing the inflammed tissue. The data shows that the drug alone has a genuine impact in controlling the disease, what has to be observed is how plasma in combination with the drug fares.

Figure 17:
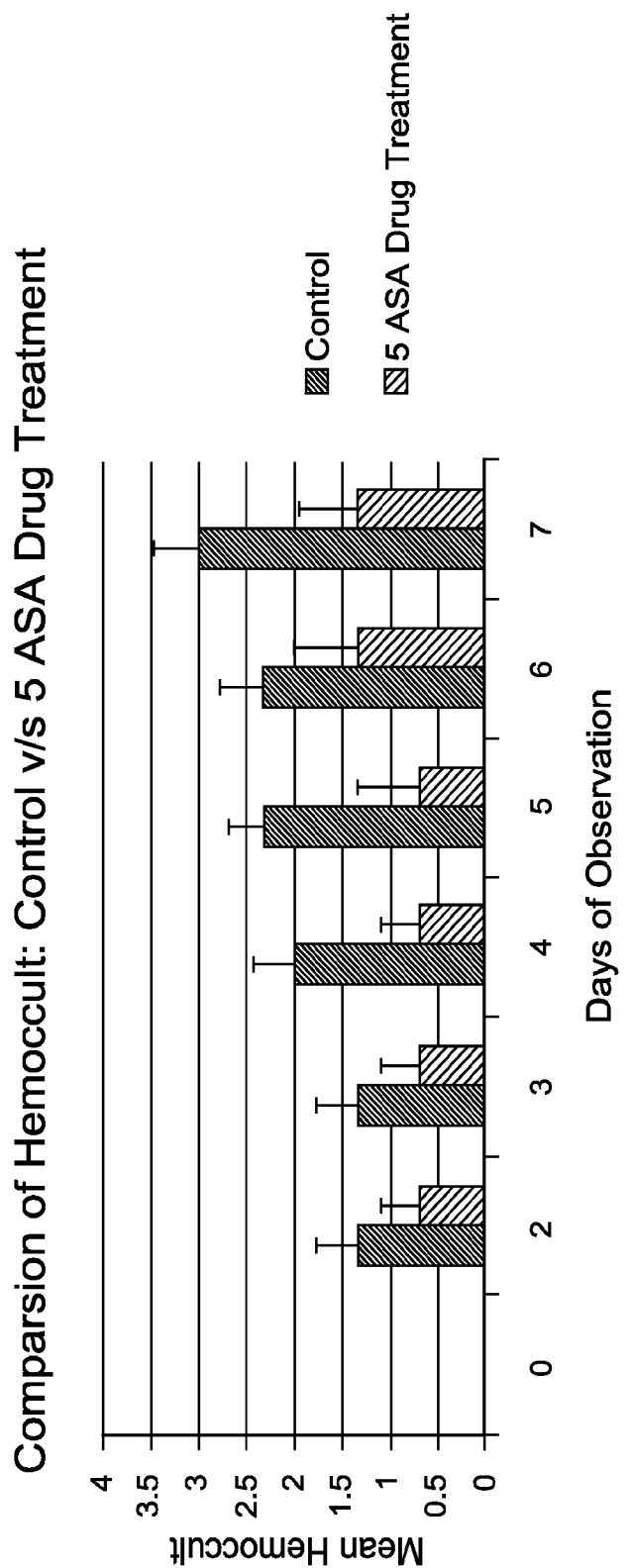

FIG. 17 is a graph showing a comparison of hemoccult between a control group and a group receiving a combined plasma and 5-ASA treatment. As discussed earlier, a desired aspect of the present study was to determine the affect of, if any, the plasma has in treating colitis when used in conjunction with a drug treatment. As indicated by the graph, the data shows that the combination treatment was more effective than the drug or plasma as stand alone. The bars show a statistical significance in the two groups as plasma and 5-ASA reduce the disease as compared to the control group on days 5 and 7.

Without intending to be bound to any particular theory, the above data suggest that non-thermal plasma alone in graded doses did not cause any detected damage to the tissue or the animal based on Evan's Blue extravasation. The study seemed to show for the first time that plasma in graded doses can be used safely in vivo without any collateral damage. Further, the data seems to indicate that non-thermal plasma did not adversely affect the animals and did not increase the progress of the disease. In fact, the data showed that the use of non-thermal plasma reduced the rate of disease progression as compared to no treatment. During testing, all three doses of non-thermal plasma reduced the DAI. However, 30 second dose of cold plasma showed most significant disease reduction based on the DAI scored. Additionally, the data suggests that the combination of non-thermal plasma and drug treatment, such as 5-ASA, may be more effective in controlling the disease. A combination therapy of 5-ASA and cold plasma showed that there is a significant therapeutic relevance when it comes to adding plasma to the drug in controlling colitis in the DSS model during the induction phase.

While the embodiments have been described in connection with the preferred embodiments of the various figures, it is to be understood that other similar embodiments may be used or modifications and additions may be made to the described embodiment for performing the same function without deviating therefrom. Therefore, the disclosed embodiments should not be limited to any single embodiment but rather should be construed in breadth and scope in accordance with the appended claims.

What is claimed:

1. A method for treating an enteric disease comprising:
   determining a location for treating the enteric disease within a patient;
   placing a probe proximate to the location, wherein the probe is configured to generate a non-thermal plasma upon application of a potential;
   applying a potential to the probe to generate the non-thermal plasma, wherein the non-thermal plasma comes in contact with the location; and
   removing the potential after a period of time to end treatment.

2. The method of claim 1, wherein the enteric disease is Crohn's disease or ulcerative colitis.

3. The method of claim 1, wherein the probe is comprised of:
   a first conduit comprising a lumen and a tip;
   a first electrode disposed within the lumen of the first conduit;
   a second electrode comprised of a metal conduit disposed within the first conduit;
   an insulator disposed within the lumen of the first conduit, the insulator configured to electrically insulate the first electrode from the second electrode; and
   a gas channel disposed between the outer surface of the metal conduit and the inner surface of the first conduit, the gas channel being capable of feeding a gas from a gas source to the tip, wherein when the potential is applied, the gas is ionized to produce the non-thermal plasma.

4. The method of claim 3, wherein the first conduit is flexible.

5. The method of claim 3, wherein the first conduit is a plastic or glass.

6. The method of claim 3, wherein the gas is compressed air.

7. The method of claim 1, wherein the period of time is four seconds, thirty seconds, or 60 seconds.

8. The method of claim 1, wherein the potential is about 0.5 kV to about 1 kV.

9. The method of claim 1, wherein a pulse duration of the potential is 50 ms.

10. The method of claim 1, wherein the power of a pulse of the potential is about 0.1 W to 0.2 W.

11. The method of claim 1, wherein the treatment continues for 7 days.

12. The method of claim 1, further comprising providing a drug to supplement the plasma.

13. The method of claim 1, wherein the drug is 5-Amino-Salicylic Acid.

14. The method of claim 1, wherein the treatment location is the mucosa and sub-mucosa of the colon.

15. The method of claim 1, wherein placing a probe proximate to the treatment location comprises inserting the probe through a patient's anus.

16. An apparatus for treating an enteric disease, comprising:
   a first conduit comprising a lumen and a tip, the first conduit being flexible;
   a first electrode disposed within the lumen of the first conduit;
   a second electrode comprised of a metal conduit disposed within the first conduit;
   an insulator disposed within the lumen of the first conduit, the insulator configured to electrically insulate the first electrode from the second electrode; and
   a gas channel disposed between the outer surface of the metal conduit and the inner surface of the first conduit, the gas channel being capable of feeding a gas from a gas source to the tip, wherein when the potential is applied, the gas is ionized to produce the non-thermal plasma.

17. The apparatus of claim 16, wherein the first conduit is a plastic or glass.

18. The apparatus of claim 16, wherein the gas is compressed air.

19. The apparatus of claim 16, wherein the period of time is four seconds, thirty seconds, or 60 seconds.

20. The apparatus of claim 16, wherein the potential is about 0.5 kV to about 1 kV.

21. The apparatus of claim 16, wherein a pulse duration of the potential is 50 ms.

22. The apparatus of claim 16, wherein the power of a pulse of the potential is about 0.1 W to 0.2 W.

* * * * *